United States Patent [19]

Badmin et al.

[11] 4,305,934
[45] Dec. 15, 1981

[54] PYRETHROID PESTICIDAL COMPOSITIONS

[75] Inventors: John S. Badmin, Isle of Sheppey; Barry J. Mears, Sittingbourne, both of England

[73] Assignee: Shell Oil Company, Houston, Tex.

[21] Appl. No.: 121,628

[22] Filed: Feb. 14, 1980

[51] Int. Cl.³ .................... A01N 57/00; A01N 37/34; A01N 37/10
[52] U.S. Cl. .................................. 424/210; 424/304; 424/308
[58] Field of Search ............... 424/210, 304, 308, 309

[56] References Cited

U.S. PATENT DOCUMENTS

| | | | |
|---|---|---|---|
| 3,591,662 | 7/1971 | Lorenz et al. | 260/940 |
| 3,666,789 | 5/1972 | Itaya et al. | 260/468 |
| 3,689,648 | 9/1972 | Lorenz et al. | 424/210 |
| 3,835,176 | 9/1974 | Matsuo et al. | 424/304 |
| 3,911,055 | 10/1975 | Lorenz et al. | 424/210 |
| 3,979,424 | 9/1976 | Searle et al. | 424/308 |
| 3,996,244 | 12/1976 | Fujimoto et al. | 260/332.2 A |
| 4,024,163 | 5/1977 | Elliott et al. | 260/347.4 |
| 4,046,799 | 9/1977 | Kameswaran et al. | 424/308 |
| 4,058,622 | 11/1977 | Fujimoto et al. | 424/308 |
| 4,161,537 | 7/1979 | Katsuda et al. | 424/304 |
| 4,199,595 | 4/1980 | Berkelhammer et al. | 424/304 |
| 4,217,302 | 8/1980 | Anderson et al. | 424/308 |
| 4,225,533 | 9/1980 | Henrick | 424/308 |
| 4,263,287 | 4/1981 | Dennis | 424/200 |

FOREIGN PATENT DOCUMENTS 862133 6/1978 Belgium .
865114 9/1978 Belgium .

Primary Examiner—Douglas W. Robinson

[57] ABSTRACT

The invention provides pesticidal compositions containing the compound of formula

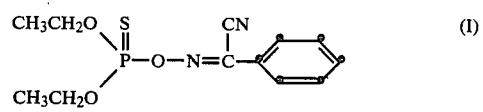

known as phoxim, and pyrethroid insecticides of formula

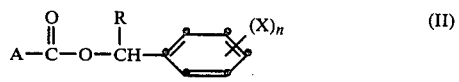

wherein A is an optionally-substituted aralkyl, alkyl, cycloalkyl or arylaminoalkyl group, R is hydrogen, cyano or ethynyl, X is alkyl, alkenyl, aralkyl or aryloxy, and n is 1 to 5, especially cypermethrin, permethrin and fenvalerate, methods of preparing the compositions and methods of combating pests at a locus by applying the compositions to the locus.

The pesticidal compositions have surprising synergistic activity against acarids.

2 Claims, No Drawings

PYRETHROID PESTICIDAL COMPOSITIONS

BACKGROUND OF THE INVENTION

1. Field of the Invention

This invention relates to new pesticidal compositions comprising phoxim and certain pyrethroids and to a method of using such compositions to combat pests.

2. Description of the Prior Art

Certain oxime phosphorothioates pesticides are disclosed in U.S. Pat. Nos. 3,591,662 and 3,689,648 which correspond to Belgian Pat. No. 678,139. On the other hand, there are litterally hundreds of articles and patents directed to synthetic pyrethroids, and in particular to their use as insecticides. Examples of compounds of diverse chemical structures which have been found to demonstrate pyrethroid-like activity are shown in U.S. Pat. Nos. 3,835,176, 3,996,244, 4,024,163, 4,161,537, and Belgian Pat. Nos. 862,133 and 865,114. For certain uses, an increase in the pesticidal spectrum of either the oxime phosphorothioates or the pyrethroid compounds would be desirable.

SUMMARY OF THE INVENTION

The invention provides a pesticidal composition which comprises:

(a) the compound of formula

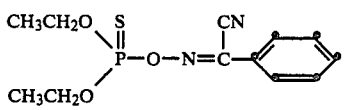

hereinafter referred to as phoxim; and (b) a pyrethroid insecticide having the following general formula:

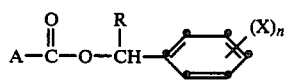

wherein A is an optionally substituted aralkyl, alkyl, cycloalkyl, or arylaminoalkyl group, R is hydrogen, cyano or ethynyl, X is alkyl, alkenyl, aralkyl or aryloxy, and n is 1 to 5.

An alkyl, cycloalkyl or alkenyl group represented by A or X preferably contains up to 6 carbon atoms, and an aralkyl or aryloxy group represented by A or X preferably contains up to 10 carbon atoms and each aryl is monocyclic.

It should be understood that the compound of the general formula II may be present in the form of any one of its pesticidally-active optical or geometric, for example cis-trans, isomers, or in the form of a mixture of isomers, for example a racemate, diastereoisomer pair or enantiomer pair. A mixture of two or more compounds according to the general formula II may be present.

When A represents an optionally-substituted cycloalkyl group, it preferably represents a cyclopropyl group of general formula:

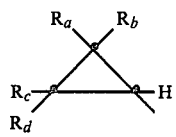

wherein $R_a$ and $R_b$ both represent an alkyl group having from 1 to 6 carbon atoms, especially a methyl group, or a halogen atom, especially a chlorine, bromine or fluorine atom; or $R_a$ and $R_b$ together represent an alkylene group having from 2 to 6, especially 3, carbon atoms; or when $R_a$ represents a hydrogen atom then $R_b$ represents an alkenyl group having from 2 to 6 carbon atoms, especially an isobutenyl group, or a haloalkyl group having from 2 to 6 carbon atoms and from 1 to 3 chalorine and/or bromine atoms, especially a monochlorovinyl, monobromovinyl, dichlorovinyl or dibromovinyl group; $R_c$ and $R_d$ both represent an alkyl group having 1 to 6 carbon atoms, especially a methyl group; or $R_c$ and $R_d$ together represent an alkylene group having from 2 to 6, especially 3, carbon atoms. Preferably, $R_a$ and $R_b$ both represent a methyl group or a chlorine atom, or $R_a$ and $R_b$ together represent an alkylene group containing 3 carbon atoms, or when $R_a$ represents a hydrogen atom then $R_b$ represents an isobutenyl group or a monochlorovinyl, monobromovinyl, dichlorovinyl or dibromovinyl group; and $R_c$ and $R_d$ both represent methyl groups or $R_c$ and $R_d$ together represent an alkylene group containing 3 carbon atoms.

When A in the general formula I represents an optionally- substituted aralkyl group, it preferably represents a substituted benzyl group of the general formula:

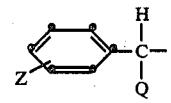

wherein Z represents a halogen, preferably chlorine, atom, or an alkoxy or haloalkoxy group of 1 to 4 carbon atoms, for example, a methoxy, difluoromethoxy or trifluoromethoxy group, and Q represents an alkyl group of 1 to 6 carbon atoms, especially a branched-chain group, for example, an isopropyl group. Preferably the group Z is in the 4-position of the benzene ring.

When A represents an optionally substituted arylaminoalkyl group, it preferably represents a substituted anilinomethyl group of general formula:

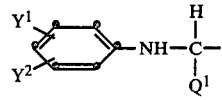

wherein $Y^1$ and $Y^2$ each independently represents a halogen, preferably chlorine, atom, or an alkyl or haloalkyl group of 1 to 4 carbon atoms, for example a trifluoromethyl group, and $Q^1$ represents an alkyl group of 1 to 6 carbon atoms, especially a branched-chain group, for example, an isopropyl group. Preferably $Y^1$ is a chlorine atom in the 2-position on the benzene ring and $Y^2$ is a trifluoromethyl group in the 4-position on the benzene ring.

Preferably n represents 1 and X represents a phenoxy or a benzyl group, especially a 3-phenoxy or 3-benzyl group.

The most preferred pyrethroid insecticides for use in the pesticidal composition according to the invention have the general formula II wherein A is alpha-isopropyl-4-chlorobenzyl, 2,2,3,3-tetramethylcyclopropyl, 2-(2,2-dichlorovinyl)-3,3-dimethylcyclopropyl, or 2-(2,2-dibromovinyl)-3,3-dimethylcyclopropyl; R is hydrogen or cyano; and n is 1 and X is 3-phenoxy. Especially preferred are the compounds known as cypermethrin, permethrin and fenvalerate whose formulae are given in the Example herein.

The weight ratio of phoxim to the pyrethroid insecticide is preferably in the range 5:1 to 1:200, more preferably in the range 1:1 to 1:100 and especially 1:1 to 1:40.

Phoxim may be prepared by the method disclosed in Belgian Patent No. 678,139.

The mixture of phoxim and the pyrethroid insecticides produces a surprising synergistic effect, for example with respect to acarid pests, particularly mites, for example, *Tetranychus urticae*, the glasshouse red spider mite. The invention therefore also provides a method of combating pests at a locus which comprises applying to that locus a pesticidal composition according to the invention.

The pesticidal composition according to the invention preferably also comprises a carrier, especially at least two carriers, at least one of which is a surface-active agent.

This invention also provides a process for preparing a pesticidal composition which comprises bringing a compound of formula I and a pyrethroid insecticide of formula II into association with at least one carrier therefor.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements, for example, carbon and sulfur; natural and synthetic resins, for example, coumarone resins, polyvinyl chloride and styrene polymers and copolymers; solid polychlorophenols; bitumen, waxes, for example, beeswax, paraffin wax, and chlorinated mineral waxes; and solid fertilizers, for example, superphosphates.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosene and light mineral oils; chlorinated hydrocarbons, for example, carbon tetrachloride, perchloroethylene and trichloroethane. Mixtures of different liquids are often suitable.

Pesticidal compositions are often formulated and transported in a concentrated form which is subsequently diluted by the user before application. The presence of small amounts of a carrier which is a surface-active agent facilitates this process or dilution.

A surface-active agent may be an emulsifying agent, a dispersing agent or a wetting agent, it may be nonionic or ionic. Examples of suitable surface-active agents include the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may, for example, be formulated as wettable powders, dusts, granules, solutions, emulsifiable concentrates, emulsions, suspension concentrates and aerosols. Wettable powders usually contain 25, 50 or 75% w of active ingerdient and usually contain, in addition to solid inert carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilizers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilizers, penetrants and corrosion inhibitors. Suspension concentrates are usually compounded so as to obtain a stable, non-sedimenting, flowable product and usually contain 10–75% w active ingredient, 0.5–5% w of dispersing agents, 0.1–10% w of suspending agents such as protective colloids and thixotropic agents, 0–10% w of other penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise-like" consistency.

The compositions of the invention may also contain other ingredients, for example, other compounds possessing pesticidal, herbicidal or fungicidal properties.

The following example illustrates the invention.

EXAMPLE

Activity of Pyrethroid/Phoxim Mixtures Against *Tetranychus urticae* (glasshouse red spider mite)

The acaricidal activities against *Tetranychus urticae* of Phoxim, the pyrethroid insecticide of formula

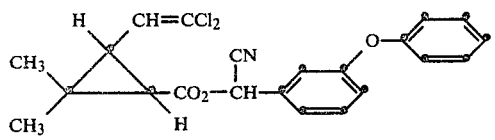

known as cypermethrin, the pyrethroid insecticide of formula

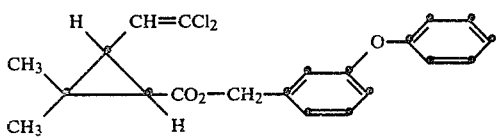

known as permethrin, the pyrethroid of insecticide of formula

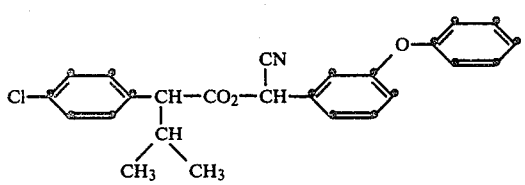

known as fenvalerate, and mixtures of phoxim with each of these three pyrethroid insecticides, were assessed by the following method.

The compounds and mixtures were formulated as solutions or suspensions in water containing 20% by weight of acetone and 0.05% by weight of Triton X-100 (trademark) as wetting agent. The resulting compositions contained 0.4% by weight of the compound or mixture to be tested, and were subsequently diluted to produce compositions containing various concentrations. Leaf discs cut from french bean plants were sprayed with the compositions and left for $\frac{1}{2}$ to 1 hour drying period. Each leaf disc was then inoculated with 10 red spider mites and mortality counts made 24 hours after innoculation. From these results the $LC_{50}$'s (the lethel concentration in weight percentage of active material in the compositions required to kill 50% of the mite population) were calculated.

Toxicity indices were then calculated using the following formula:

$$\text{Toxicity Index} = \frac{LC_{50} \text{ of standard}}{LC_{50} \text{ of compound or mixture}} \times 100$$

The standard used was ethyl parathion.

The joint action of the two active components of a mixture was analysed by the method of Yun-Pei Sun and E. R. Johnson, Journal of Economic Entomology, 1960, Vol. 53 no. 5, pp. 887–892. A coefficient of co-toxicity of a mixture is given by:

$$\text{coefficient of co-toxicity of mixture} = \frac{\text{Actual Toxicity Index of Mixture}}{\text{Theoretical Toxicity Index of Mixture}} \times 100$$

The theoretical toxicity index of a mixture is equal to the sum over both components of the percentage of each individual compound present in the mixture multiplied by its respective toxicity index.

A coefficient and co-toxicity of a mixture near 100 indicates the probability of similar action by the two compounds; independent action usually gives a coefficient less than 100; and a coefficient significantly above 100 strongly indicates synergism.

The results are illustrated in the following Table:
The results are illustrated in the following Table:

TABLE

| Test Compounds | $LC_{50}$ | Coefficient of co-toxicity |
| --- | --- | --- |
| phoxim | 0.0017 | |
| cypermethrin | 0.22 | |
| permethrin | 0.17 | |
| fenvalerate | 0.17 | |
| phoxim/cypermethrin (1:30 mixture) | 0.035 | 155 |
| phoxim/permethrin (1:40 mixture) | 0.025 | 200 |
| phoxim/fenvalerate (1:40 mixture) | 0.034 | 145 |

The coefficients of co-toxicity obtained indicate synergism in the mixtures tested.

We claim:

1. An acaricidal composition comprising as active ingredients
(a) the compound of formula

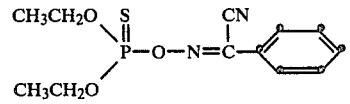

and
(b) a pyrethroid insecticide of the formula

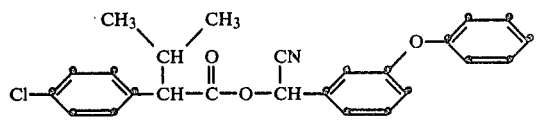

in a ratio of (a) to (b) of 1 to 40.

2. A method of combating acarid pests at a locus which comprises applying to the locus an acaricidally effective amount of a composition according to claim 1.

* * * * *

UNITED STATES PATENT AND TRADEMARK OFFICE
CERTIFICATE OF CORRECTION

PATENT NO. : 4,305,934

DATED : December 15, 1981

INVENTOR(S) : JOHN S. BADMIN and BARRY J. MEARS

It is certified that error appears in the above-identified patent and that said Letters Patent are hereby corrected as shown below:

Cover Sheet

After section [22], insert

-- [30]    Foreign Application Priority Data

February 21, 1979 [GB]  United Kingdom.....79/06111 --.

Signed and Sealed this

Sixteenth Day of March 1982

[SEAL]

Attest:

Attesting Officer

GERALD J. MOSSINGHOFF

Commissioner of Patents and Trademarks